United States Patent [19]

Dwyer et al.

[11] Patent Number: 5,489,441
[45] Date of Patent: Feb. 6, 1996

[54] METHOD FOR SUPPRESSING IMMUNE RESPONSE ASSOCIATED WITH PSORIASIS, CONTACT DERMATITIS AND DIABETES MELLITUS

[75] Inventors: Donard S. Dwyer, Shreveport, La.; Kristin Esenther, Ashland, Mass.

[73] Assignee: Procept, Inc., Cambridge, Mass.

[21] Appl. No.: 109,232

[22] Filed: Aug. 19, 1993

Related U.S. Application Data

[63] Continuation-in-part of Ser. No. 817,536, Jan. 7, 1992, Pat. No. 5,238,689.
[51] Int. Cl.$^6$ ............................ A01N 59/16; A61K 33/24
[52] U.S. Cl. ............................ 424/617; 424/719; 514/885
[58] Field of Search ................................. 424/617, 719

[56] References Cited

U.S. PATENT DOCUMENTS 5,308,623  5/1994  Fues et al. ............................ 424/617

OTHER PUBLICATIONS

Kapus et al., "Ruthenium Red Inhibits Mitochondrial Na+ and K+ Uniports Induced by Magnesium Removal", *J. of Biological Chemistry*, 265(30): 18063–18066 (1990).

Missiaen et al., "Ruthenium Red and Compound 48/80 Inhibit the Smooth–Muscle Plasma–Membrane . . . ", *Biochimica et Biophysica Acta*, 1023: 449–454 (1990).

Tsuruo et al., "Growth Inhibition of Lewis Lung Carcinoma by an Inorganic Dye, Ruthenium Red", *Gann*, 71:151–154 (1980).

Dornand et al., "PCP and Analogs Prevent the Proliferative Response of T Lymphocytes . . . ", *Biochemical Pharmacology*, 36(22): 3929–3936 (1987).

Broekemeier et al., "Cyclosporin A Is a Potent Inhibitor of the Inner Membrane Permeability Transition in Liver Mitochondria", *J. of Biological Chemistry*, 264(14):7826–7830 (1989).

*Primary Examiner*—Rebecca Cook
*Attorney, Agent, or Firm*—Hamilton, Brook, Smith & Reynolds

[57] ABSTRACT

This invention relates to the use of Ruthenium Red as an immunosuppressive agent to prevent or significantly reduce graft rejection in organ and bone marrow transplantation. Ruthenium Red can also be used as an immunosuppressant drug for T lymphocyte mediated autoimmune diseases, such as diabetes. Furthermore, Ruthenium Red may be useful in alleviating psoriasis and contact dermatitis.

9 Claims, 3 Drawing Sheets

METHOD FOR SUPPRESSING IMMUNE RESPONSE ASSOCIATED WITH PSORIASIS, CONTACT DERMATITIS AND DIABETES MELLITUS

RELATED APPLICATION

This application is a continuation-in-part application of U.S. Ser. No. 07/817,536, filed Jan. 7, 1992, the entire teachings of which are incorporated herein by reference.

BACKGROUND OF THE INVENTION

Replacement of defective or severely injured tissues and organs has been a medical objective as long as medicine has been practiced. Grafts from an individual to himself almost invariably succeed, and are especially important in the treatment of burn patients. Likewise, grafts between two genetically identical individuals almost invariably succeed. However, grafts between two genetically dissimilar individuals would not succeed without immunosuppressive drug therapies. The major reason for their failure is a T cell mediated immune response to cell-surface antigens that distinguish donor from host.

Immunosuppressive agents are also indicated in the treatment of autoimmune diseases such as rheumatoid arthritis or type I diabetes mellitus. One particular condition worth mentioning here is psoriasis. This disease is characterized by erythematous patches of skin accompanied by discomfort and itching. Hyperplasia of the epidermis involving proliferation of keratinocytes is also a hallmark feature of psoriasis. An inflammatory component is suggested by: (i) the finding of lymphocytic infiltration of epidermis, and (ii) the fact that immunosuppressive agents such as cyclosporin and corticosteriods have beneficial effect on the disease.

A number of drugs are currently being used or investigated for their immunosuppressive properties. Among these drugs, the most commonly used immunosuppressant is cyclosporin A. However, usage of cyclosporin has numerous side effects such as nephrotoxicity, hepatotoxicity and other central nervous system disorders. Thus, there is presently a need to investigate new immunosuppressive agents that are less toxic but equally as effective as those currently available.

SUMMARY OF THE INVENTION

This invention relates to the use of Ruthenium Red as an immunosuppressive agent to prevent or significantly reduce graft rejection in organ and bone marrow transplantation. Ruthenium Red can also be used as an immunosuppressant drug for T lymphocyte mediated autoimmune diseases, such as diabetes.

In another aspect of this invention, other diseases with suspected inflammatory components, such as psoriasis and contact dermatitis, can be treated with Ruthenium Red to alleviate symptoms associated with these disease states.

DETAILED DESCRIPTION OF THE INVENTION

Figure 1:
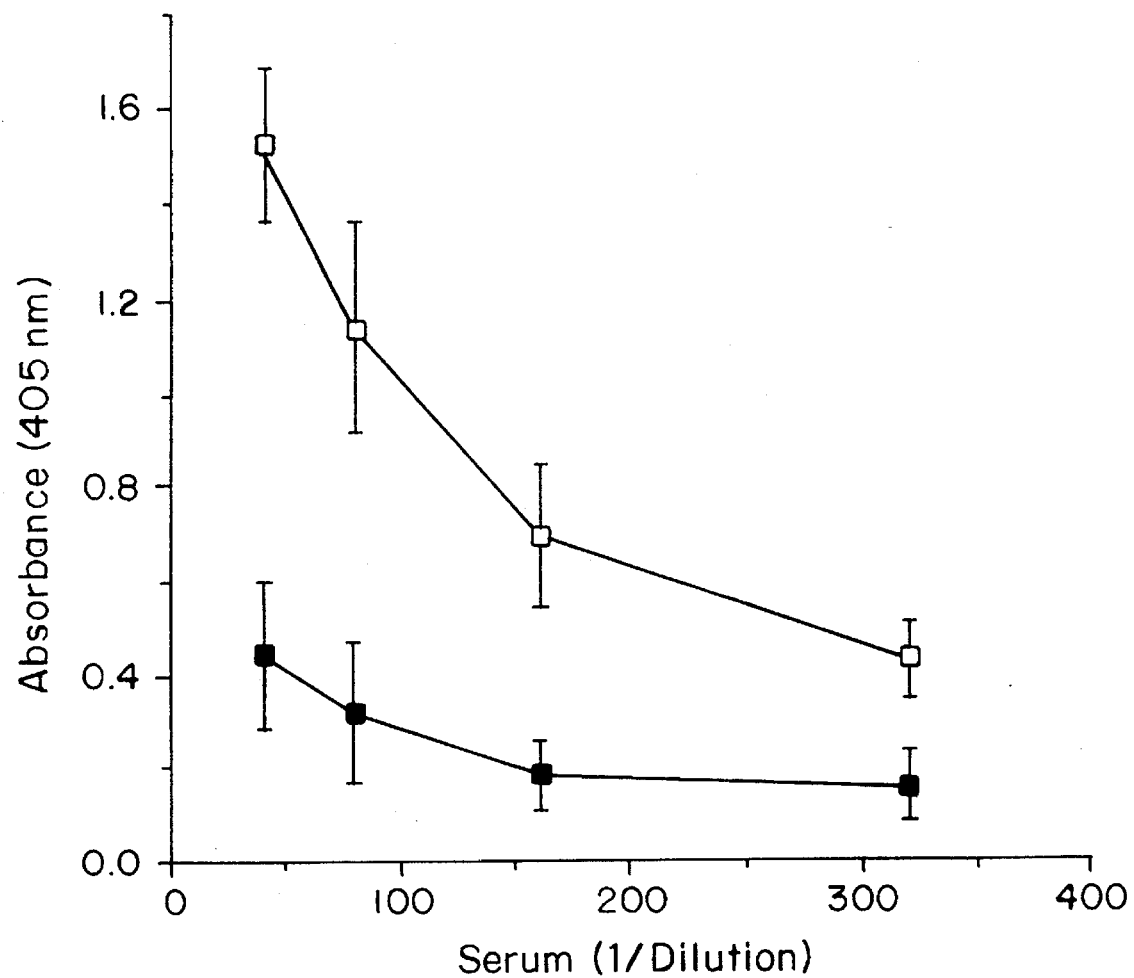
FIG. 1 illustrates absorbance values obtained through an ELISA assay. The upper plot represents antibody levels generated in a group of mice following immunization with Cytochrome C (open box). The lower plot depicts the reduced antibody levels observed in Ruthenium Red treated mice (closed box). The data indicate that the compound acts as an immunosuppressive agent in vivo.

This invention is based upon the discovery that Ruthenium Red can inhibit antigen specific T lymphocyte proliferation in vitro, and act as an immunosuppressive agent in vivo in mice for both antibody and cell mediated immune responses. The data suggest that Ruthenium Red has potential use as an immunosuppressant to reduce undesirable immune responses in humans. Ruthenium Red can be used to facilitate organ transplantation, and to treat human autoimmune disorders where the specific activation of T cells is responsible for, or contributes to the pathology and progression of the diseases, such as diabetes.

It has been shown herein that Ruthenium Red protected a small group of female non-obese diabetic (NOD) mice from insulin dependent diabetes mellitus (IDDM), a disease that normally occurs at high frequency in the female of this inbred mouse strain.

Psoriasis has two main clinical features which characterize the disease; an autoimmune or inflammatory infiltration of the epidermis, and hyperproliferation of keratinocytes. It has been shown herein that when applied topically, Ruthenium Red can penetrate murine skin and block contact hypersensitivity to a specific antigen. Ruthenium Red has also been shown to inhibit keratinocyte proliferation in vitro. Based upon these findings, Ruthenium Red can be used to alleviate the symptoms associated with psoriasis and contact dermatitis. Abnormalities in mitochondrial function in psoriatic epidermal cells may also be corrected by Ruthenium Red treatment since it has also been shown to affect mitochondria.

The effects of topical application in mice suggest that in humans also, topical application of Ruthenium Red in a cream or ointment could deliver locally immunosuppressive concentrations of the drug without significant systemic exposure. Topical application may be the ideal way to deliver the compound in psoriasis and perhaps other inflammatory skin diseases such as contact dermatitis and pemphigus vulgaris. Herein are described experiments which demonstrate in vitro that Ruthenium Red can penetrate human skin sufficiently to achieve T cell immunosuppressive doses.

Ruthenium Red is an inorganic hexavalent polycationic dye that has been used in histology and electron microscopy to stain certain complex polysaccharides. These dyes have also been shown to affect calcium ion transport in the smooth muscle plasma membrane of pig stomach cells and in the mitochondria of rat liver cells. See Missiaen et al., *Biochimica et Biophysica Acta,* 1023:449–454 (1990) and Kapus et al., *J. of Biological Chemistry,* 265(30):18063–18066 (1990). In addition, Ruthenium Red has been shown to possess certain anti-tumor properties, as demonstrated by growth inhibition of Lewis lung carcinoma in mice treated with the dye. Tsuro et al., *Gann,* 71:151–154 (1980).

It has now been discovered that Ruthenium Red possesses immunosuppressive activity as confirmed through a drug screen. Specific T cell proliferation was measured in response to antigen exposure in the presence or absence of Ruthenium Red. It was found that Ruthenium Red inhibited T cell proliferation by 50% ($IC_{50}$) at a concentration of about 200 nM. This compares favorably with cyclosporin A, which has an $IC_{50}$ at 15nM. In an in vitro toxicity study, Ruthenium Red was found to be nontoxic to a variety of cell lines when tested at the same concentrations that markedly inhibit T cell activation.

The dye is known to bind a wide variety of materials, but more importantly, it binds to components of cell membranes. Ruthenium Red has been shown to inhibit plasma membrane $Ca^{2+}$ pump. It is believed that the dye interacts at the cytoplasmic site of the $Ca^{2+}$ pump; however, its mode of action is still not fully understood. It is known that $Ca^{2}+$ is an important mediator of T cell activation. Transient elevation of cytoplasmic $Ca^{2+}$ occurs shortly after triggering of T cells by a variety of signals and is necessary for activation of the interleukin-2 (IL-2) gene.

Ruthenium Red can be administered orally, parenterally (e.g. intramuscularly, intravenously, subcutaneously), topically, nasally or via slow releasing microcarriers in dosage formulations containing a physiologically acceptable vehicle and optional adjuvants and preservatives. Suitable physiologically acceptable vehicles include saline, sterile water, creams, ointments or solutions.

The specific dosage level of active ingredient will depend upon a number of factors, including biological activity of Ruthenium Red, age, body weight, sex, general health, severity of the particular disease to be treated and the degree of immune suppression desired, as well as appropriate pharmacokinetic properties. It should be understood that Ruthenium Red can be administered to mammals other than humans for immunosuppression of mammalian autoimmune diseases.

Ruthenium Red can be administered in combination with other drugs to boost the immunosuppressive effect. Compounds that can be coadministered include steroids (e.g. methyl prednisolone acetate), NSAIDS and other known immunosuppressants such as azathioprine, 15-deoxyspergualin, cyclosporin and related molecules. Dosages of these drugs will also vary depending upon the condition and individual to be treated.

The assay used to measure T cell growth inhibition was a human peripheral blood lymphocyte (PBL) proliferation assay using standard procedures known in the art. PBL's were chosen due to their known ability to proliferate in the presence of antigens derived from herpes simplex virus (HSV), Rubella or tetanus toxoid (TT). PBL growth inhibition was measured in terms of Ruthenium Red's ability to interfere with antigen induced lymphocyte proliferation.

The invention will be further illustrated by the following non-limiting Examples:

EXAMPLE 1—PBL ANTIGEN SPECIFIC PROLIFERATION ASSAY

Ruthenium Red was purchased from Sigma Chemical Company, and dissolved in water at a 1 mg/ml concentration for the stock solution. The stock solution of the dye was diluted over a range of 1:400 to 1:100,000 for the PBL inhibition assay.

The lymphocytes were prepared by first separating them from the blood samples of several donors by Ficoll gradient separation as described by standard procedure known in the art. The isolated lymphocytes were then grown in RPMI 1640 medium containing 5% human AB serum, glutamine (2 mM), penicillin/streptomycin, 50 μ/ml/50 ng/ml sodium pyruvate (1 mM) and HEPES buffer (10 mM).

For assay purposes, PBL's were incubated at a density of $10^5$ per 200 μl of medium per well of a 96-well plate.

Concentrated tissue culture supernatants containing antigens derived from HSV infected cells were diluted 1:1000 to induce T cell proliferation.

In separate studies, Tetanus toxoid was used as a stimulating antigen at a concentration range of 0.4–4 LF/ml.; provided by Massachusetts Department of Public Health, Boston, Mass.

The test wells containing PBL's, were exposed to one of the three stimulating antigens (i.e., HSV, Rubella or TT derived antigens), along with various dilutions of the Ruthenium Red solutions, as shown in Table 1. The supernatant from uninfected cells (obtained from Microbix Biosystems, Inc. of Toronto, Canada) were used as a control for the response to HSV.

Subsequently, HSV antigen/Ruthenium Red exposed PBL's were pulsed with 1 μCi/well of $^3$H-thymidine on day 4 whereas the Rubella/dye and TT/dye exposed cells were pulsed on day 5 using a standard procedure known in the art. The cells were then harvested 16 hours later onto a glass fiber filter using a PHD harvester from Cambridge Technology, Boston, Mass. Thymidine incorporation was measured by liquid scintillation counting using a Beta counter (Pharmacia, Inc., Piscataway, N.J.).

The results of the assay are shown in Table 1. The table shows that a 2.5 μg/ml concentration of Ruthenium Red generally inhibited proliferation by 90%. The molar concentration to obtain $IC_{50}$ was estimated to be approximately 200 nM. The inhibition values in Table 1 represent the mean of 5 separate experiments.

In addition, Ruthenium Red was shown to be non-toxic at levels effective as an immunosuppressant agent. The compounds were tested for toxicity in the following cell lines: Jurkat (T cell lymphoma); K562 (erythroleukemia); Hs294T (melanoma cells); U-937 (monocytes from histiocytic lymphoma) and M-EBV (Epstein-Farr virus-transformed β-cells).

TABLE 1

Inhibition of human T cell proliferation by Ruthenium Red

| Concentration, μg/ml (μM) | | % Inhibition |
|---|---|---|
| 2.5 | (3.18) | 96 |
| 1.0 | (1.27) | 89 |
| 0.2 | (0.25) | 60 |
| 0.1 | (0.13) | 31 |
| 0.01 | (0.01) | 17 |

To obtain a more complete picture of the range of responses effected by Ruthenium Red, the ability of this compound to inhibit alloreactivity was examined. A summary of these results is presented in Table 2.

TABLE 2

Inhibition of alloreactivity by Ruthenium Red

| Concentration, μ/ml (μM) | % Inhibition |
|---|---|
| 2.5 (3.18) | 92 |
| 1.0 (1.27) | 85 |
| 0.2 (0.25) | 77 |
| 0.1 (0.13) | 69 |

Alloreactivity was measured by stimulating T cells from one donor with inactivated lymphocytes from a second donor. The inhibition values represent the mean of 4 separate determinations. These data confirm that Ruthenium Red has broad immunosuppressive properties in vitro.

EXAMPLE 2—ASSAY OF IL-2 STIMULATED PBL PROLIFERATION

It was discovered that the proliferative response induced directly in PBL's by IL-2 alone can be inhibited by this compound (Table 3). For these studies, human peripheral blood lymphocytes (PBL's) were incubated in vitro with varying concentrations of IL-2 and in the presence or absence of Ruthenium Red (0.2 μg/ml). After 3 days of culture, $^3$H-thymidine was added for 16 hr, cells were harvested, and the filters counted.

TABLE 3

Ruthenium Red blocks IL-2-mediated T cell proliferation

| IL-2 (U/ml) | Ruthenium Red | $^3$H-thymidine uptake (cpm) | % Inhibition |
|---|---|---|---|
| 0 | − | 543 | − |
| 100 | − | 31,175 | − |
| 1 | − | 36,559 | − |
| 100 | + | 3,839 | 88 |
| 1 | + | 2,805 | 92 |

These findings suggest that Ruthenium Red cannot only prevent T cell activation (like cyclosporin) but can also abrogate the response to IL-2 which make this compound superior to cyclosporin, FK506 and related compounds.

EXAMPLE 3—ASSAY OF THE KINETICS OF THE INHIBITION OF T CELL ACTIVATION BY RUTHENIUM RED

In another study, T cells were activated with HSV-1 as described before and the Ruthenium Red (1 μg/ml) was added either at the start of culture (time 0) or after various delays. Data in Table 4 reveal that the compound can be added as late as 20 hours after triggering with antigen and still produce maximal inhibition, indicating that Ruthenium Red most likely effects signal transduction pathways rather than early recognition events at the cell surface.

TABLE 4

Kinetics of the inhibitory response to Ruthenium Red

| Time of addition (hr) | % Inhibition |
|---|---|
| 0 | 95 |
| 1 | 97 |
| 2 | 96 |
| 4 | 92 |
| 20 | 86 |
| 33 | 58 |

EXAMPLE 4—ASSAY OF CYTOPLASMIC $CA^{2+}$ LEVELS DURING T CELL ACTIVATION

To uncover the mode of action of Ruthenium Red, additional experiments were performed. Because it is known that this compound effects $Ca^{2+}$ levels in cells, we examined whether Ruthenium Red prevents the rise in intracellular $Ca^{2+}$ that accompanies T cell activation. The $Ca^{2+}$-sensitive dye, Fluo-3AM (Molecular Probes, Inc., Eugene, Oreg.), can be used to detect intracellular $Ca^{2+}$. For these studies, transfected Jurkat T cells were incubated with Fluo-3AM (1 μM) for one hour at room temperature. The cells were then washed three times and incubated in 1 ml volumes ($5\times10^5$ cells) with various agents to trigger T cell activation and thus $Ca^{2+}$ uptake. Ruthenium Red was added at a concentration of 1 μg/ml (1.27 μM).

The results in Table 5 show a major reduction in the percentage of cells staining positively with the dye, indicative of reduced levels of cytoplasmic $Ca^{2+}$. Thus, Ruthenium Red prevents the rise in intracellular $Ca^{2+}$ in response to T cell activation.

TABLE 5

Calcium influx into activated human T cells is diminished by Ruthenium Red

| | Ruthenium Red | % Fluorescent cells |
|---|---|---|
| Blank | − | 1.3 |
| Calcium ionophore | − | 84.6 |
| Activation (anti-CD2) | − | 47.0 |
| Activation (anti-CD2) | + | 17.2 |

EXAMPLE 5—ASSAY OF THE ANTIBODY RESPONSE TO CYTOCHROME C IN MICE

Because the in vitro data appeared very promising, Ruthenium Red was tested for in vivo immunosuppressive properties. B10.A mice were treated with Ruthenium Red (dissolved in water) by intraperitoneal injection (4 mg/kg) daily for two days prior to immunization with cytochrome c (50 μg per mouse in complete Freund's adjuvant), and were treated for an additional 12 days after challenge with antigen. On day 23 after immunization, the animals were bled and sera were evaluated for specific antibodies to cytochrome c in an enzyme-linked immunosorbent assay (ELISA). The data are presented in FIG. 1. The absorbance values obtained in the ELISA have been plotted against the dilution of serum containing specific antibodies. The upper plot represents antibody levels in the group treated with water, whereas the lower plot depicts the ELISA values for the Ruthenium Red treated mice. Overall, treatment of mice with Ruthenium Red led to a 70% reduction in antibody levels when compared to the control mice who received water.

To extend these findings, the experiments were repeated with larger groups of mice and, in addition, the in vitro proliferative response of T cells to the immunizing antigen was evaluated. For these studies, B10.A mice were treated with Ruthenium Red as before and immunized with cytochrome c. On day 7 after challenge with antigen, draining lymph nodes were removed and single cell suspensions of lymphocytes were prepared. The lymphocytes were counted to estimate overall yields and were cultured in vitro with antigen (100 μg/ml) for three days prior to addition of tritiated thymidine to quantitate proliferation. The results are shown in Table 6.

TABLE 6

In vivo effects of Ruthenium Red
on T cell responses of BIO.A mice

| Mouse # | Ruthenium Red | Cell Yield | Specific proliferation (cpm) |
|---|---|---|---|
| 1 | − | $19 \times 10^6$ | 21,902 |
| 2 | − | $6.7 \times 10^6$ | 66,320 |
| 3 | − | $7 \times 10^6$ | 19,484 |
| 14 | + | $0.26 \times 10^6$ | * |
| 16 | + | $0.81 \times 10^6$ | * |
| 17 | + | $16 \times 10^6$ | 22,236 |

* Insufficient cells to determine specific proliferation.

Mice treated with water exhibited normal enlargement of lymph nodes and on average yielded about $11 \times 10^6$ cells per mouse. In all cases, there was a good proliferative response to cytochrome c. In contrast, two of the three mice treated with Ruthenium Red showed no enlargement of lymph nodes following immunization and the total cell yields were 1/20th that observed in the controls. There were too few cells to assess T cell proliferation in vitro as indicated by the asterisk. The third mouse responded normally to cytochrome c.

The remaining mice in this study continued on their assigned treatment and were bled on day 23, as in the original pilot study, and sera were tested for specific antibodies in the ELISA. The data has been expressed as the mean of the endpoint dilution. The data have been summarized in Table 7.

TABLE 7

Ruthenium Red suppresses
in vivo production of specific antibody

| Group | High Responders | 1/Mean Titer |
|---|---|---|
| Control | 8/9 | 40,106 ± 11,384 |
| Ruthenium Red | 2/6 | 18,613 ± 13,020 |

Mice were considered high responders if their antibody titer against cytochrome c was greater than 1:5,120.

The control mice produced high levels of antibody to cytochrome c; 8 of 9 had a titer greater than 1:5000. On the other hand, the mice treated with Ruthenium Red gave an inferior response; only 2 of the 6 mice had titers greater than 1:5000. These findings are in keeping with both the original pilot study and the in vitro proliferative data that suggested that two thirds of the mice show a greatly reduced response to antigen upon treatment with Ruthenium Red. Thus, the in vitro data demonstrating the immunosuppressive properties of Ruthenium Red have been confirmed by these in vivo studies.

EXAMPLE 6—CONTACT HYPERSENSITIVITY ASSAY

Figure 2:
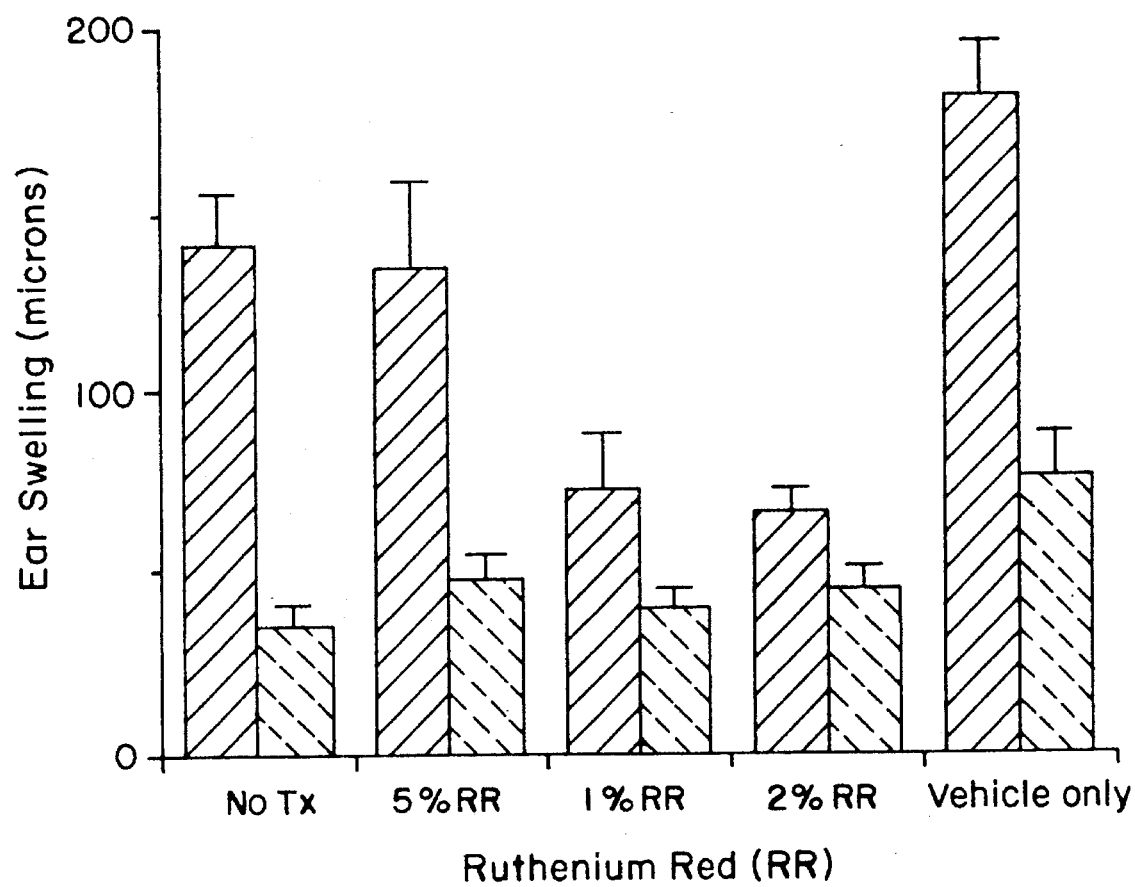
FIG. 2 shows a graphic illustration of the inhibition by Ruthenium Red of the elicitation of contact hypersensitivity (CHS) in sensitized mice. The broken stippled bars represent nonsensitized mice challenged at day 8 and the solid stippled bars represent mice sensitized at day one and then challenged at day 8. Contact hypersensitivity involves a T lymphocyte mediated inflammatory reaction in the skin, and the ability of Ruthenium Red to inhibit it is an indicator that the compound may also reduce the severity of inflammation in human skin disorders such as contact dermatitis and psoriasis.

The ability of Ruthenium Red to inhibit contact dermatitis when applied topically to mice was determined by exposing mice to a known toxic irritant. C57Bl/6mice were sensitized by painting a 5% solution of trinitrochlorobenzene (TNCB) on the shaved dorsum. Seven days later, mice were challenged by applying a 1% solution of TNCB to the ears. A localized immune hypersensitivity developed beneath the skin, giving rise to edema and erythema at the site of exposure. The immunological response was predominantly due to T lymphocytes. The treated mice then received topical administration of Ruthenium Red in petrolatum (at a 0.5, 1 or 2% final concentration) 1 hours and 12 hours later. After 24 hours, ear thickness was measured using a spring loaded engineer's micrometer. For comparison, control mice were given vehicle alone at the same two time points. The data have been expressed as the size (in microns) of the ear and represent the averages of 5 mice per group. It is clear from FIG. 2 that pronounced swelling of the ear occurs only after pre-sensitization by hapten; more importantly, Ruthenium Red treatment produces a dose-dependent reduction in that swelling. The edema is a consequence of a hypersensitivity reaction mediated by T lymphocytes. Therefore, Ruthenium Red must be preventing this local inflammatory response. Because the Ruthenium Red was applied topically, the data also indicate transdermal absorption of the material which is a critical requirement for therapy of psoriasis by topical application of compound.

EXAMPLE 7—HUMAN EPIDERMAL PENETRATION ASSAY

Figure 3:
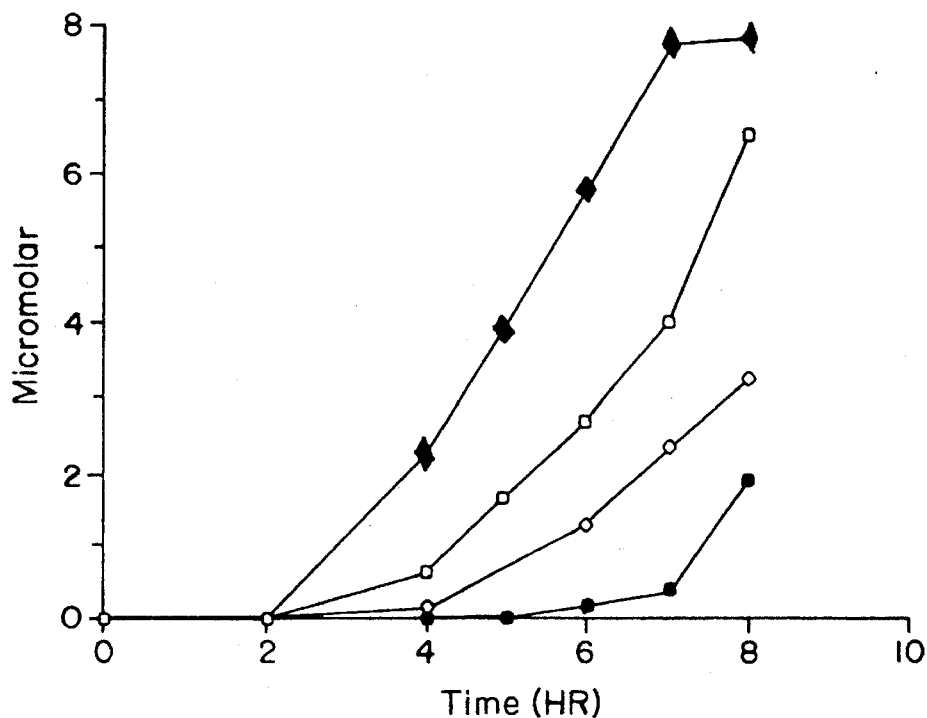
FIG. 3 shows a graphic illustration of the rate of diffusion of Ruthenium Red across a human skin explant in a tissue culture chamber when the compound was applied in petrolatum to one surface of the skin section. The data are as follows: 2% Ruthenium in hydrated petrolatum (HP) HP-1 (open box); 2% Ruthenium Red in HP-2 (closed diamond); 2% Ruthenium Red in phosphate buffered saline (PB51) (closed box) and 2% Ruthenium Red in PBS-2 (open diamond). The data indicate that a sufficient amount of the compound can cross the skin to achieve immunosuppressive concentrations at the opposite surface.

The ability of Ruthenium Red to be absorbed transdermally by human skin was investigated in vitro using a segment of explanted skin stretched across a tissue culture chamber so as to form a barrier between two compartments. Ruthenium Red in phosphate buffered saline (PBS) or hydrated petrolatum (HP) at a concentration of two per cent (w/v) was applied to the epidermal surface exposed in one compartment, and transport across the skin was measured using spectroscopy to determine the amount of the compound arriving in the second compartment after regular time intervals. As shown in FIG. 3, when applied in hydrated petrolatum, sufficient Ruthenium Red had crossed the skin sample by 5–7 hours to achieve a concentration of approximately 4 micro-molar in the second compartment. This concentration is greater than that required to inhibit the antigen-specific proliferation of human T cell in vitro (see Table 2), and the data therefore suggest that human skin is sufficiently permeable to allow Ruthenium Red to achieve an active concentration at the potential site of the inflammatory immune reactions involved in psoriasis and contact dermatitis.

EXAMPLE 8—INHIBITION OF KERATINOCYTE PROLIFERATION

Figure 4:
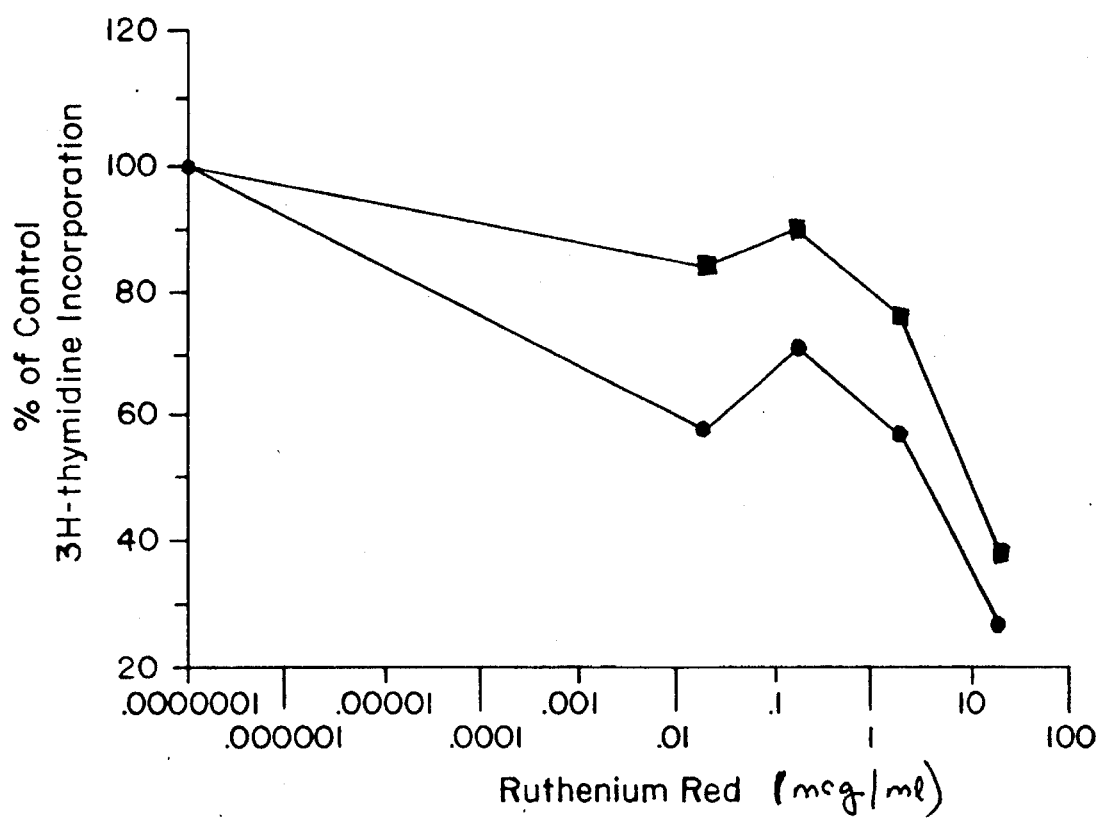
FIG. 4 shows the inhibition of the in vivo proliferation of the PAM 212 keratinocyte cell line by Ruthenium Red in two similar experiments. The data is an indicator that the compound may be effective in reducing hyperplasia of the epidermis in psoriasis.

The effects of Ruthenium Red on the proliferation of a murine transformed keratinocyte cell line, PAM212, was measured. The cells were added to 96 well flat-bottom plates in RPMI medium (100 μl) containing 5% fetal bovine serum, non-essential amino acids, L-glutamine, sodium pyruvate and HEPES, at a concentration of $2 \times 10^5$ cells per well. Next, 100 μl of either medium alone or medium containing various dilutions of Ruthenium Red were added to the cells. After 72 hours, proliferation was assessed by measuring $^3$H-thymidine incorporation into the cells. The results of these studies are depicted in FIG. 4. The addition of Ruthenium Red to the cultures is accompanied by a marked reduction in the growth of the PAM 212 line. In two repetitions of the experiment, there appears to be a biphasic effect whose exact meaning is unclear at this time. Nevertheless, even at concentrations of compound as low as 50 ng/ml there is significant inhibition of keratinocyte proliferation.

EXAMPLE 9—PREVENTION OF THE AUTOIMMUNE DISEASE OF INSULIN DEPENDENT DIABETES MELLITUS

Insulin dependent diabetes mellitus (IDDM) otherwise known as juvenile onset diabetes is thought to result from the immunologically specific destruction of the insulin producing pancreatic islet cell by auto-immune T cells. Knowledge of the disease derives to a large extent from the study of the non-obese diabetic NOD inbred mouse that is genetically predisposed to developing IDDM at approximately 30 weeks of age in 70–90 per cent of females and 30–50 percent of males. Female (NOD) mice were treated with water or Ruthenium Red dissolved in water by intraperitoneal injection (4 mg/kg) every other day for three weeks starting at 6 weeks of age, and for a further three weeks starting at 15 weeks of age. Data in Table 8 indicate that the treatment with Ruthenium Red suppressed the onset of IDDM compared with treatment with water alone. Mice were observed up to approximately 32 weeks of age. Diabetic mice were initially identified by elevated glucose levels in the urine, and the presence of disease confirmed by the measurement of blood glucose levels using standard procedures known in the art. Blood glucose values of greater than 10 mM indicated diabetes.

TABLE 8

Evaluation of Ruthenium Red in the Prevention of diabetes in NOD mice

| Treatment | Mice with diabetes by 32 weeks of age |
| --- | --- |
| Water | 3/6 |
| Ruthenium Red | 0/4 |

EQUIVALENTS

Those skilled in the art will recognize, or be able to ascertain, using no more than routine experimentation many equivalents to the specific embodiments of the invention described herein. Such equivalents are intended to be encompassed by the following claims:

We claim:

1. A method for alleviating psoriasis and symptoms associated therewith resulting from a T-lymphocyte mediated immune response in a mammal comprising administering Ruthenium Red in a physiologically acceptable vehicle to an afflicted site on the mammal, thereby suppressing a T-lymphocyte mediated immune response associated with psoriasis.

2. The method of claim 1, whereby the Ruthenium Red is topically administered to the afflicted site.

3. The method of claim 1 wherein the Ruthenium Red is administered as a cream, ointment or solution.

4. The method of claim 1 wherein the mammal is a human.

5. A method for reducing hyperplasia of the epidermis resulting from a T-lymphocyte mediated immune response in a mammal caused by psoriasis comprising administering Ruthenium Red in a physiologically acceptable vehicle to an afflicted site on the mammal, thereby suppressing a T-lymphocyte mediated immune response associated with psoriasis.

6. A method for alleviating contact dermatitis and symptoms associated therewith resulting from a T-lymphocyte mediated immune response in a mammal comprising administering Ruthenium Red in a physiologically acceptable vehicle to an afflicted site on the mammal, thereby suppressing a T-lymphocyte mediated immune response associated with contact dermatitis.

7. The method of claim 6 wherein the Ruthenium Red is topically administered.

8. The method of claim 6 wherein the Ruthenium Red is administered as a cream, ointment or solution.

9. The method of claim 6 wherein the mammal is a human.

* * * * *